(12) United States Patent
Berentsveig et al.

(10) Patent No.: US 9,226,495 B2
(45) Date of Patent: Jan. 5, 2016

(54) DISINFECTION AEROSOL, METHOD OF USE AND MANUFACTURE

(75) Inventors: Vladimir Berentsveig, New South Wales (AU); Ron Weinberger, New South Wales (AU)

(73) Assignee: SABAN VENTURES PTY LIMITED, Alexandria, New South Wales (AU)

( * ) Notice: Subject to any disclaimer, the term of this patent is extended or adjusted under 35 U.S.C. 154(b) by 566 days.

(21) Appl. No.: 13/321,796

(22) PCT Filed: May 21, 2010

(86) PCT No.: PCT/AU2010/000609
§ 371 (c)(1),
(2), (4) Date: Jun. 26, 2012

(87) PCT Pub. No.: WO2010/132948
PCT Pub. Date: Nov. 25, 2010

(65) Prior Publication Data
US 2012/0263800 A1 Oct. 18, 2012

(30) Foreign Application Priority Data
May 22, 2009 (AU) .................................. 2009902310

(51) Int. Cl.
| A01N 59/00 | (2006.01) |
| A01N 59/06 | (2006.01) |
| A01P 1/00 | (2006.01) |
| A01N 25/06 | (2006.01) |
| A61L 2/22 | (2006.01) |
| A61L 9/14 | (2006.01) |

(52) U.S. Cl.
CPC . *A01N 25/06* (2013.01); *A61L 2/22* (2013.01); *A61L 9/14* (2013.01); *A61L 2202/25* (2013.01); *A61L 2209/11* (2013.01); *A61L 2209/211* (2013.01)

(58) Field of Classification Search
CPC ....... A01N 25/06; A01N 59/00; A01N 59/04; A61L 2/22; A61L 9/14
See application file for complete search history.

(56) References Cited

U.S. PATENT DOCUMENTS

| 4,899,914 | A | 2/1990 | Schweigl et al. |
| 2003/0143110 | A1 | 7/2003 | Kritzler et al. |
| 2004/0208781 | A1 | 10/2004 | Hayashi et al. |
| 2005/0008531 | A1 | 1/2005 | Parkhurst et al. |
| 2005/0169953 | A1 | 8/2005 | Flashinski |
| 2005/0197252 | A1 | 9/2005 | Yamashita |
| 2007/0048175 | A1 | 3/2007 | Tichy et al. |
| 2007/0060478 | A1 | 3/2007 | Witschel et al. |
| 2007/0184016 | A1* | 8/2007 | Macinga et al. ........... 424/78.27 |
| 2008/0233005 | A1 | 9/2008 | Tichy et al. |
| 2008/0251547 | A1 | 10/2008 | Ruiz De Gopegui et al. |
| 2008/0318775 | A1 | 12/2008 | Basel et al. |
| 2010/0092574 | A1* | 4/2010 | Sweeny ....................... 424/616 |

FOREIGN PATENT DOCUMENTS

| GB | 1 514 216 | 6/1978 |
| JP | H04-144672 | 5/1992 |
| JP | 2003-175917 | 6/2003 |
| JP | 2004-042040 | 2/2004 |
| JP | 2006-087343 | 4/2006 |
| WO | WO 2006/076406 A2 | 7/2006 |

OTHER PUBLICATIONS

International Search Report from the Australian Patent Office for International Application No. PCT/AU2010/000609, mailing date Aug. 16, 2010.
Supplementary European Search Report issued in corresponding Application No. EP 10 77 7237, dated Nov. 3, 2014, 6 pages.

* cited by examiner

*Primary Examiner* — Mina Haghighatian
(74) *Attorney, Agent, or Firm* — Finnegan, Henderson, Farabow, Garrett & Dunner, L.L.P.

(57) ABSTRACT

Aerosols comprising droplets dispersed in a carrier gas, wherein at least some of the droplets contain an antagonist effective to inactivate a biocide are provided. The droplets may contain the biocide and the antagonist that reacts with the biocide to render it harmless. The biocide is used for disinfection or sterilization, and the nature and concentration of the antagonist is selected, or means are provided, to ensure that the time required for the antagonist to render the biocide ineffective is longer than the time required for the biocide to be effective for a desired level of disinfection or sterilization. Methods of manufacture of aerosols are also provided.

20 Claims, 17 Drawing Sheets

DISINFECTION AEROSOL, METHOD OF USE AND MANUFACTURE

FIELD OF THE INVENTION

The present invention relates to methods and compositions for disinfecting or decontaminating exposed surfaces or spaces which may be infected with bacteria, fungi, viruses, fungal or bacterial spores, prions, and the like infectious species.

"Sterilization" has been defined in WO2007/014435 as a process capable of achieving a log 6 reduction in concentration of spores. "Disinfection" is a similar process, the difference being that it results in a lesser degree of biocidal effect, particularly on bacterial spores. "Sterilization" includes "disinfection" and "disinfection/sterilization" is an abbreviation for "disinfection and/or sterilization". In general the words disinfect and sterilize and related words may be taken to indicate a reduction or treatment of virus, bacteria, or other living organisms but also includes decontamination of surfaces that are exposed to harmful chemicals often used in chemical warfare, such as by oxidation of the chemical. Disinfection or sterilization is required to be effective and not necessarily complete. For convenience, in the present application, "disinfect", "sterilize", disinfect and sterilize, disinfect/sterilize" and "disinfect or sterilize" is used generally to refer to the treatment of living organisms or decontamination where harmful chemicals are present.

The invention is applicable both to the disinfection/sterilization of instruments and articles placed in small disinfection chambers, biological safety cabinets, isolators, glove boxes, incubators, materials airlocks and the like. The invention is applicable for disinfection/sterilization of food containers or the like and manufacturing machinery and is also applicable for the disinfection of very large spaces.

The invention will primarily be herein described, by way of example only, with particular reference to the problems associated with disinfection/sterilization of spaces and surfaces found in hospitals, for example the walls, floor, ceiling and content surfaces in an operating theatre or hospital ward but is not limited to such environments.

The invention is equally applicable for disinfection or sterilization of surfaces bounding, or contained in, large spaces such as shopping malls, factories, mail sorting spaces, subways, sports stadiums, shipping containers, aircraft interiors or the like. Exposed surfaces may be exemplified by surfaces of walls or partitions defining the space, by work surfaces or machinery surfaces, air conditioning ducts, or other surfaces which are interior or can be enclosed or partly enclosed, at least temporarily, such as hospital beds.

The invention is also applicable for disinfection/sterilization of occluded surfaces.

The invention is also applicable in open or external spaces for example for protection of troops and others from chemical warfare attack in which they are exposed to Biological Warfare Agents such as anthrax, ebola, Marburg virus, plague, cholera, tularemia, brucellosis, Q fever, machupo, *coccidioides mycosis*, glanders, melioidosis, *shigella*, Rocky Mountain spotted fever, typhus, psittacosis, yellow fever, Japanese B encephalitis, Rift Valley fever, smallpox or other microorganisms and for protection of civilians similarly exposed during terrorist attacks or the like.

BACKGROUND OF THE INVENTION

Any discussion of the prior art throughout the specification should in no way be considered as an admission that such prior art is widely known or forms part of common general knowledge in the field.

In recent years there has been a marked increase in the number and variety of micro-organisms which have been identified as particularly problematic in hospital environments. Increased labour costs have reduced the frequency and intensity with which walls, floors, ceilings and other surfaces are scrubbed with disinfectants and/or sterilizing agents. Although this treatment still occurs to a somewhat restricted extent in operating theaters, it is more usual for such treatment to be limited to surfaces within a 2 meter radius of an operating table. Scrub-down treatment is rarely extended these days to general wards or public areas. Moreover there are many surfaces within scrubbed areas such as the interior of locks, the guards covering castor wheels, the underside of doors, the occluded surface of hinges which are not satisfactorily treated by scrub-down and may harbour organisms. In addition in some operating theaters, electronic equipment such as computers and the like include fans which blow cooling air through equipment and carry particles which may harbour microorganisms into equipment housing where microorganisms may multiply on interior surfaces.

It has been proposed to disinfect both small and large spaces and enclosing surfaces with biocidal gases such as ozone or chlorine dioxide which are oxidative or corrosive and toxic, or with biocidal gases such as ethylene oxide and aldehydes, such as glutaraldehyde or formaldehyde. However such biocides are all extremely toxic, hazardous to use and may leave potentially harmful residues on surfaces. Steam is sometimes used but is hazardous to the operator and detrimental to many materials and much equipment because of the high temperatures involved, and as it leaves dense moisture on the surface it may lead to rusting or deterioration.

In recent years the use of hydrogen peroxide or peracetic acid as a disinfectant has become greatly preferred. Prior to the 1990s these peroxides were considered too unstable and hazardous to allow fumigation with the vapours. Nevertheless, various proposals have been made to use hydrogen peroxide in the vapour phase for disinfection/sterilization. Mostly vapour phase systems have been applicable to small volume chambers such as sterilizers that can be evacuated since the vapours are more effective at very low pressures or as plasmas (e.g. Schmidt U.S. Pat. No. 4,863,688). At the end of the treatment cycle, residual hydrogen peroxide vapour is pumped out by the vacuum pump and exhausted to atmosphere directly or via a catalytic destroyer which decomposes any residual peroxide vapour into harmless oxygen and water. In older vapour based instrument reprocessing systems it was proposed to remove surface contamination by use of rinse water, which risked water damage and introduced a drying problem since drying is both energy intensive and of long duration. Disadvantageously, water rinsing imposes a need for a water supply and drainage system which is a major disadvantage in some locations.

Peroxide vapours have also been proposed for use at atmospheric pressure but in that case longer treatment times are generally involved than in vacuum systems and efficacy against bacterial spores has been shown to be limited. After treatment in small scale peroxide vapour systems, air is circulated through the chamber and any residual peroxide is either flushed directly into the atmosphere through a HEPA-filter, or is flushed into the atmosphere via a catalytic destructor so that the peroxide is catalysed to oxygen and water prior to disposal. In some recirculating systems the flow may be diverted after the treatment and recirculated by an air pump though a catalytic destroyer placed in parallel with the treatment circuit until peroxide is eliminated (e.g. Hill U.S. Pat. No. 7,238,330; U.S. Pat. No. 6,953,549).

Others have proposed to use peroxide aerosols (rather than vapour) as the biocidal agent for sterilization/disinfection of small chambers. Aerosols have a number of major advantages over vapour including that much higher concentration density of active species is obtainable at atmospheric pressure and the need for costly vacuum equipment is eliminated. In some such cases the aerosol flow may be diverted through a catalytic destructor after the treatment cycle is completed to remove any peroxide residues (see applicant's commonly owned WO 2007/014436 and WO2007/014438).

Both peroxide vapour and peroxide aerosol systems have also been proposed for disinfection/sterilization or decontamination of larger spaces. In such case it mostly appears that any residue is merely flushed into the external environment. Ronlan in U.S. Pat. No. 6,500,465 proposed the use of a thermo fogger (pulse jet fogger) to provide a high density aerosol (aerosol droplet diameter less than 50 microns) of peracetic acid or hydrogen peroxide suitable for disinfecting at 100% relative humidity, but does not discuss peroxide disposal. Adiga U.S. Pat. No. 7,326,382 discloses something similar but likewise does not discuss peroxide disposal. Applicant's commonly owned WO2007/014437 (Erickson) and WO2007/014435 (Berentsveig et al.) have also used aerosols for large scale disinfection purpose. Erickson envisaged a portable catalytic destructor unit that could be moved from chamber to chamber and used to remove excess peroxide from a treated chamber, saying "The reservoir, nebuliser, fan, and heater may be combined in a portable unit which can be moved from chamber to chamber, and if desired a separate air drying or air conditioning system may be made portable for use in the same chamber as the nebuliser or may be combined with the nebuliser unit", while Berentsveig vented residual peroxide directly or optionally via a catalytic destructor. Residual peracetic acid suffers from the additional disadvantage of unacceptable odour While such stable mists of aqueous biocides, preferably hydrogen peroxide, can be employed at atmospheric pressure and above and avoid the need for vacuum equipment and are more easily adaptable to disinfection or fumigation of very large spaces, elimination of residual hydrogen peroxide remains a significant problem.

For example in sterilizing food containers with peroxide, even trace amounts of hydrogen peroxide can affect the flavor of the product or result in other undesirable changes, such as a change in the color of the product. Food packaging regulations now limit hydrogen peroxide residues on containers to a maximum of 0.5 ppm in the United States. Surface residues in operating theaters or on surgical instruments should be below 1 ppm. To achieve such levels by blowing or sucking air even though small chamber volumes for sterilizing instruments or the like can add significantly to process times, but to do so through a room size volume of 50-100 cu meters requires huge capital equipment and energy costs, especially when the incoming air needs also to be HEPA-filtered to maintain sterility. The volume of air in the room needs to be replaced more than ten times. The removal step thus adds greatly to treatment times because the residual balance of peroxide reduces asymptotically. A significant time (hours in a large building) is required to remove the last few ppm of sterilant and the space may not be safely re-habitable until this step is completed. For example a Steris VHP1000 vapour system takes up to 6 hrs to treat a 56 $m^3$ room. The larger the volume of space treated the more difficult the removal problem becomes as the time for removal increases asymptotically.

In recent years particular attention has been paid to spaces which have become infected as a result of acts of war or terrorism. For example in the US a number of federal buildings were thought to have been contaminated by Anthrax spores. These were treated with chlorine gas which was very damaging to the building but in addition required a long time before the chlorine could be effectively removed to a level at which the building could be made habitable. In any disinfection and or sterilization method, it is important that the overall duration of the process including both treatment with biocide and removal of biocide to a point where the space can be safely occupied be minimized.

Chemical disinfection agents such as hypochlorite solutions have in the past been proposed for deactivating biological warfare agents but such biocidal agents are themselves harmful to personnel and equipment due to corrosiveness and toxicity.

In summary peroxy compounds such as hydrogen peroxide, hydrogen peroxide complexes, and peracetic acid are preferred as agents for disinfection/sterilization of surfaces, (eg medical instruments and food processing machinery and operating tables); for disinfection/sterilization of small and large chambers and of large spaces, as well as for deactivation of biological warfare agents. Peroxide has been used both as a vapour and as an aerosol for this purpose. Although disinfection/sterilization can be achieved in very short times, removal of residual peroxide down to safe levels of below 1 ppm, preferably below 0.5 ppm is a major problem, taking an unacceptably long time, and being very costly in terms of required equipment and energy consumption. The time problem increases greatly for large volume spaces. Many other biocides also have residual toxicity or corrosive properties which renders their use impractical.

OBJECTS OF THE INVENTION

It is an object of the present invention to overcome or ameliorate at least one of the disadvantages of the prior art, or to provide a useful alternative.

It is an object of the present invention to provide a method for disinfecting or sterilizing a volume and/or surface area which avoids or ameliorates at least some of the disadvantages of the prior art. It is a further object of the invention to provide improved apparatus and improved compositions for carrying out the method.

It is an object of preferred embodiments of the invention to provide means and methods whereby the amount of dispersed chemical agent, for example a disinfection/sterilization agent, may be reduced in a comparatively short time.

It is an object of preferred embodiments to be able to disinfect/sterilize spaces and surfaces in both small chambers such as, for example, sterilizing chambers or glove boxes and large spaces such as operating theatres, wards of hospitals, cold rooms, refrigerators, vans, sea containers, factory areas and such like where disinfection is a requirement and to do so by means which allow the treatment to be conducted, including removal of biocides, to be completed quickly—in the case of habitable volumes to the level at which the space is re-inhabitable.

It is an object of very highly preferred embodiments to provide a safe and effective self inactivating biocidal aerosol. By "self inactivating" aerosol is herein meant an aerosol in which an active reagent is inactivated, neutralized, inactivated, or otherwise rendered benign (i.e. safe, harmless or free of odour).

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

BRIEF STATEMENT OF INVENTION

According to a first aspect the invention provides an aerosol comprising droplets dispersed in a carrier gas, wherein at least some of the droplets contain an antagonist effective to inactivate a biocide.

By "antagonist" is herein meant any substance which reacts with, neutralizes, renders benign, or catalyses the destruction of, or otherwise changes another substance—or acts as an intermediary in its destruction or inactivation.

In a preferred embodiment in which a peroxide (for example hydrogen peroxide) is employed as a biocide to kill microorganisms, the biocide is rendered inactive and harmless by an aerosol according to the first aspect wherein at least some droplets contain an antagonist which is for example a metal ion, enzyme or other reagent which catalyses or causes the decomposition of hydrogen peroxide to oxygen and water. This renders the peroxide harmless and makes it unnecessary to replace the air in the chamber.

Those skilled in the art will recognize that in the past hydrogen peroxide has been used in small volume liquid systems to kill microorganisms for example on contact lenses and the hydrogen peroxide has subsequently (i.e. after completion of the disinfection step) been inactivated by the addition of a suitable liquid hydrogen peroxide destroying compound, for example a catalase. In some small volume liquid systems (e.g. contact lens cleaners) a catalase has been added to a liquid peroxide solution as a tablet encapsulated in a slowly soluble encapsulant so as to dissolve in the liquid after the peroxide has completed a disinfection step.

Embodiments of the invention according to the first aspect envisage, for example, that the space within and the surfaces within a chamber into which hydrogen peroxide has been previously admitted as a vapour or aerosol, are rendered innocuous by introducing a suitable antagonist in an aerosol form. In preferred embodiments the antagonist converts any residual peroxide into water and oxygen in a short time. Those skilled in the art will appreciate that it has not previously been practiced to use a deactivator in an aerosol form. In the past in vapour and aerosol systems after all, or a sufficient proportion, of the organisms have been killed, peroxide has been removed by pumping out the chamber, blowing air through the chamber and in some cases the residual peroxide vapours or aerosols have been inactivated by passage of the pumped or blown air flow through catalytic destroyers in which the vapour or aerosol is brought into contact with solid catalysts.

It has not previously been practiced in a vapour or aerosol system to convey deactivator to the peroxide rather than convey the peroxide to the deactivator, nor to have the catalyst as an aerosol, much less to have both peroxide and an antagonist present in the same aerosol or in the same aerosol droplets.

In embodiments according to the first aspect the introduction of a mist or aerosol containing the antagonist may be delayed until after the peroxide has achieved a desired disinfection/sterilization effect. Alternatively, if the inactivation or destruction produced by the antagonist proceeds at a slow rate in comparison with the disinfection rate, the aerosol containing the antagonist may be introduced simultaneously with (or even prior to) the peroxide.

In preferred embodiments a peroxide (such as hydrogen peroxide or peracetic acid) is used as a disinfecting or sterilizing agent (biocide) and the antagonist is any suitable catalytic destructor (for example manganese or other transition metals, metal ions, metal oxides, or salts, or combinations of the foregoing; triethanolamine or other alkaline compounds; catalases; or the like).

In a preferred embodiment according to the first aspect, the antagonist effective to inactivate hydrogen peroxide is nebulised (as a liquid, solution, or liquid suspension of a very fine solid) via a first nebuliser to produce an aerosol or mist containing the antagonist. This may be introduced into a space containing a biocide, for example, hydrogen peroxide as an aerosol (previously introduced into the space) to neutralize the biocide (in the example of peroxide—producing water and oxygen) as particles in the combined mists collide and/or coalesce or condense together on surfaces. The biocide may have also have been previously introduced into the space as a liquid or a vapour. Although it is preferred to nebulise a solution of suitable antagonist (destructor), the destructor may also be produced in situ in the aerosol by reaction between precursors.

According to a second aspect the invention provides an aerosol comprising droplets dispersed in a carrier gas, and characterized in that at least some of the droplets contain a biocide; and at least some of the droplets in the aerosol contain an antagonist reactive with the biocide to render it harmless.

In preferred embodiments according to the second aspect, hydrogen peroxide (as a liquid solution) is a biocide which may be nebulised via a first nebuliser; the antagonist (as a liquid, solution or liquid suspension) may be nebulised via a second nebuliser; and the two nebulants are combined to produce an aerosol in which both droplets of the peroxide and droplets of the antagonist are suspended. The droplets of the peroxide remain effective at least until they come into contact with droplets of the antagonist, either as a result of collision, coalescence or condensation. The time lapse before the two kinds of droplets come into contact each with the other may be influenced, for example by control of respective nebulising conditions, nebulizing rate, nebulant particle size, or by electrically charging one or both kinds of droplet as they emanate from the respective nebulisers, or simply by delaying introduction of one of the components. Hydrogen peroxide is considered harmless at concentrations below 1 ppm.

According to a third aspect the invention provides an aerosol according to the second aspect wherein at least some of the droplets contain BOTH the biocide and the antagonist reactive with the biocide to render it harmless.

In this case the reaction kinetics must be controlled so that the biocide is able to be effective to kill microorganisms before it is rendered harmless by the antagonist.

According to a fourth aspect the invention provides an aerosol according to the second or third aspect wherein the biocide is used for disinfection or sterilization, and the nature and concentration of the antagonist is selected, or means are provided, to ensure that the time required for the antagonist to render the biocide ineffective is longer than the time required for the biocide to be effective for a desired level of disinfection or sterilization.

In embodiments according to the third and fourth aspect, which are highly preferred forms of the invention, the peroxide and antagonist are combined (as a liquid, solution or liquid suspension) immediately prior to being nebulised via a first nebuliser. The resulting aerosol contains droplets in which BOTH the biocide and the antagonist coexist in the same droplets. In this case it is important that the reaction of the antagonist with the agent is sufficiently slow, or is otherwise slowed, so that the agent has time to be effective before it is rendered ineffective by the antagonist. The reaction rate of the antagonist with the peroxide may be controlled by selection of an antagonist which destroys peroxide slowly in comparison with the speed with which the peroxide acts as a biocide. Alternatively the antagonist may be formed or act via an intermediate step which is slow in comparison with the disinfection/sterilization step. A further possibility is that the reaction speed of the biocide is enhanced by inclusion for example of bleach activators or the like, by selection of conditions such as concentration, temperature, humidity and/or a combination of such kinetic rate controlling measures may be adopted.

According to a fifth aspect the invention provides an aerosol comprising droplets dispersed in a carrier gas, wherein at least some of the droplets contain a biocide, and at least some of the droplets, which may be the same or different from those carrying the biocide, contain an antagonist effective to inactivate the biocide.

According to a sixth aspect the invention provides a self inactivating biocidal aerosol.

Embodiments according to the sixth aspect of the invention may be made by feeding a peroxide and a suitable catalytic destructive agent as antagonist from separate supplies as feeds to a common nebuliser input port and wherein the combination is nebulised in a predetermined ratio of peroxide to antagonist to produce an aerosol in which both components are in each droplet of the gas stream. The peroxide may be intended to produce a disinfection or sterilization effect in a chamber or room, and means are provided to ensure that the catalytic destructor also present in the aerosol is not effective to destroy the peroxide prior to the peroxide achieving a desired level of biocidal efficacy. Although in a preferred embodiment the agent and the antagonist co-exist, at least initially, in the same droplet, the biocidal agent and the antagonist may be in different droplets in the aerosol—i.e. the peroxide and antagonist may be nebulised separately and the nebulants then combined.

Other aspects of the invention relate to the method of manufacture of aerosols according to any one of the first to sixth aspects and to methods of use of aerosols according to any one of the first to sixth aspects. Aerosols according to the invention may be prepared by any suitable means. While the use of ultrasonic nebulisers is preferred, the invention may be implemented using spray jets, foggers, centrifugal devices, other atomizers, and may include aerosol cans in some applications.

Preferred embodiments of the invention significantly shorten the time required for reduction of peroxide concentration in a chamber to acceptable levels.

The invention will initially be exemplified with reference to system in which the biocide is a peroxide. Subsequently it will be exemplified with reference to other examples in which the biocide is an aerosol according to any one of the preceding aspects wherein the biocide is selected from the group consisting of biocidal oxidizing agents, quaternary ammonium compounds, aldehydes, halogenated phenols, pyrrolidones, silanols, and combinations thereof with discussion of appropriate antagonists for such biocides.

BEST MODE OF PERFORMING THE INVENTION

The invention will now be more particularly described with reference to examples.

Figure 1:
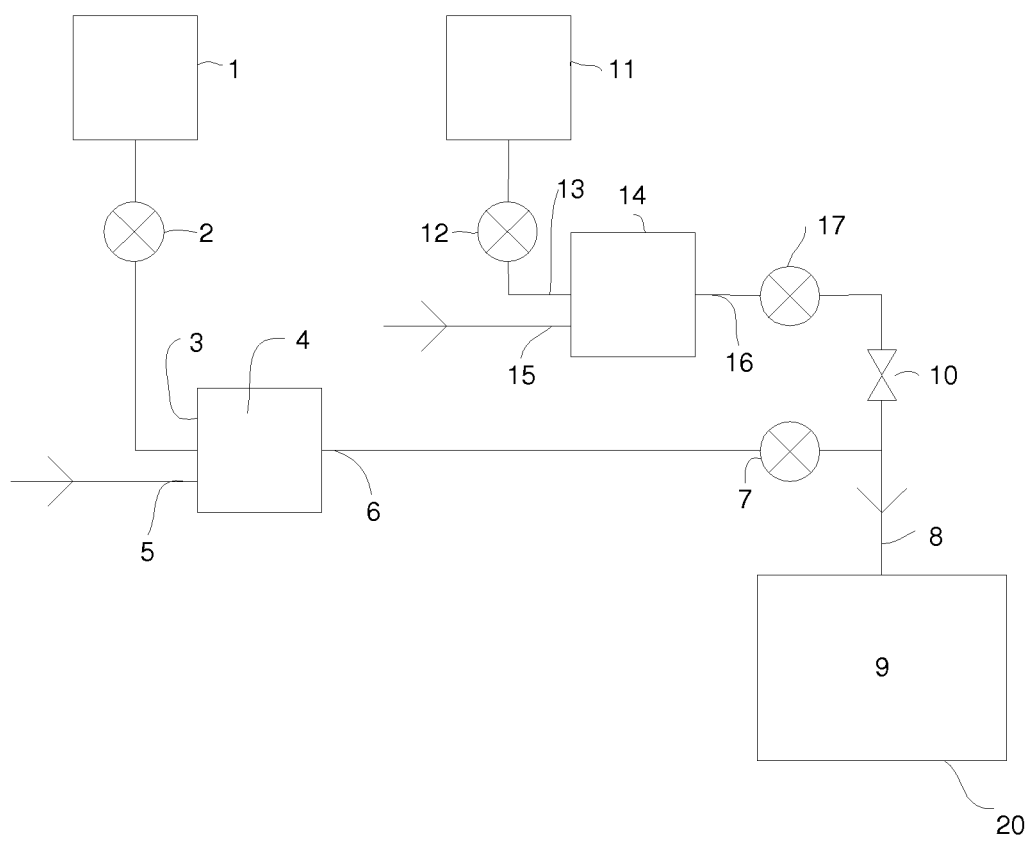
FIG. 1 is a schematic diagram useful for describing embodiments of a process according to the invention.

With reference to FIG. 1, there is shown schematically a method for manufacture and use of an aerosol according to the first aspect of the invention. In this example a chamber 9, for example a glove box, is to be sterilized prior to reuse with fresh microorganisms. A solution of 35% hydrogen peroxide is fed from a peroxide containing reservoir 1 via a valve 2 to inlet port 3 of a first nebuliser 4, which in the present example is an ultrasonic nebuliser, such as more particularly described in WO2007/014435, WO2007/014436 or WO2007/014437. Nebuliser 4 also receives a stream of carrier gas, for example air, at nebuliser gas inlet 5 and produces a microfine mist of hydrogen peroxide solution at nebuliser outlet 6 which is conducted via valve 7 and chamber inlet 8 to chamber 9. This sterilization step has been described in prior art. It takes only a few minutes to achieve a 6 log reduction of even difficult to kill microorganisms such as bacterial spores using a suitable aerosol of hydrogen peroxide in a chamber such as 8. However it may take many hours to eliminate the peroxide from the chamber by conventional means depending on its volume.

In a first embodiment according to the first aspect of the present invention after the disinfection/sterilization step is completed valve 7 is closed, and a second aerosol is produced from a solution of a peroxide antagonist or catalytic destructor such as a Mn(II) salt, or a transition metal salt, or combination of them, a catalase, or other peroxide destroying agents to be discussed in more detail hereinafter. The antagonist may include other reagents such as pH modifiers or buffers, preservatives (e.g. in the case of catalases), stabilizers, kinetics modifiers and so on. With reference to FIG. 1, the antagonist solution is contained in reservoir 11 and fed via valve 12 into inlet port 13 of a second nebuliser 14. Nebuliser 14 also receives a stream of carrier gas, for example air, at nebuliser gas inlet 15 and produces a microfine mist of the antagonist solution at nebuliser outlet 16 which is conducted via valve 17 (and optionally via a non return valve 10) to chamber inlet 8 and thus enters chamber 9. The antagonist aerosol enters the chamber as a very fine mist and reacts with any residual hydrogen peroxide in the chamber either by contact between mist particles which coalesce, or by condensation on surfaces or both. A pressure relief valve 20 or recirculation line may be provided but it is not necessary to detail such provisions for the principles of the invention to be comprehended.

Figure 2:
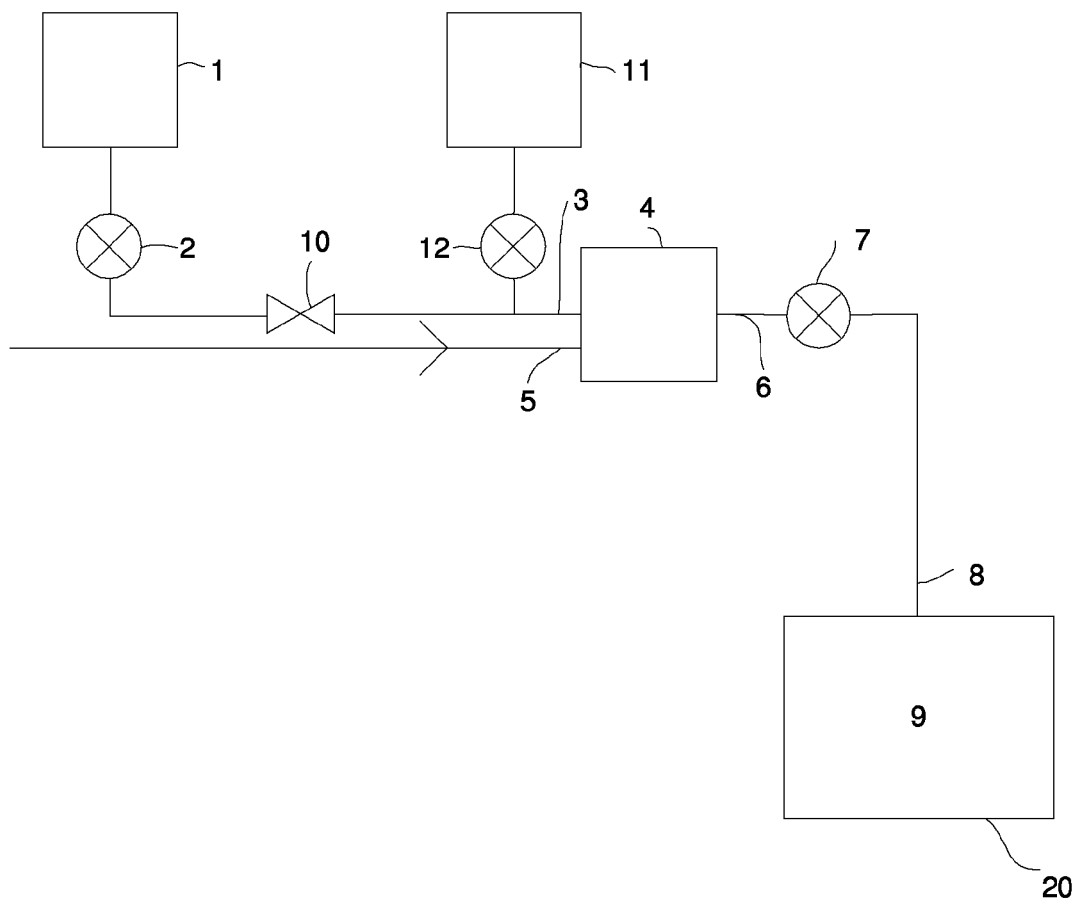
FIG. 2 is a schematic diagram useful for describing embodiments of a process according to the invention

According to a second embodiment according to the first aspect of the present invention shown in FIG. 2, wherein parts of corresponding function are identified by the same numerals as in FIG. 1, with valve 2 open and valve 12 closed, a peroxide mist may be prepared via nebuliser 4 and admitted to chamber 9 until a desired level of microorganism kill is achieved. After a desired degree of disinfection/sterilization is achieved, valve 2 may then be closed and valve 12 opened to allow antagonist to be nebulised in the same nebuliser 4 and admitted to chamber 9 to react with and eliminate residual peroxide in the chamber.

It will be understood that depending on how quickly the antagonist destroys hydrogen peroxide it may not be necessary to wait until after the hydrogen peroxide has completed a desired level of microorganism kill before admitting the antagonist aerosol to chamber 9. The antagonist may be manufactured and admitted while the peroxide is still active as a biocide—for example if there is a threshold or induction period before the antagonist reacts with the peroxide or if the rate of peroxide destruction is slow in comparison with the rate of peroxide biocidal effect. In such cases the antagonist may be admitted while the biocide is still acting on microorganisms.

In a third embodiment according to the second aspect of the invention there is provided an aerosol according to the first aspect comprising droplets dispersed in a carrier gas, wherein at least some of the droplets contain hydrogen peroxide and at least some of the droplets contain an antagonist effective to render hydrogen peroxide ineffective.

In this case apparatus similar to that of FIG. 1 may be used, but a nebulant of hydrogen peroxide 1 prepared via nebuliser 4 is combined with a nebulant of antagonist 11 prepared via nebuliser 14 and the respective nebulants are combined into a single gas stream containing droplets of peroxide and droplets of antagonist prior to admission to chamber 9. The mixing may be facilitated by a mixing chamber not shown in FIG. 1 between valves 7, 17 and chamber 9. In this case it is important that any reaction between the antagonist and the peroxide is sufficiently delayed that the peroxide can kill microorganisms to a desired level before the antagonist destroys the remaining peroxide. When the peroxide and the antagonist are in different droplets, reaction of one with the other can be delayed by electrically charging the particles oppositely, by influencing particle size and the like. However it is preferred to delay the reaction of one with the other by selection of antagonist and control of reaction kinetics as discussed below.

In a fourth embodiment according to the sixth aspect of the invention an antagonist is combined with the peroxide in each droplet to produce a self destructive biocide.

In this case apparatus similar to that shown schematically in FIG. 2 may be employed but a peroxide solution from reservoir 1 and an antagonist solution from reservoir 11 are combined either by control of valves 2 and 12 or in a liquid mixing chamber (not illustrated in FIG. 2) between those valves and nebuliser inlet 3. Thus a liquid mixture of the peroxide solution 1 with antagonist solution 11 is mixed immediately prior to being nebulised in nebuliser 4 and fed to chamber 9 via line 7. The antagonist subsequently inactivates the biocide in chamber 9.

A liquid mixing chamber (not illustrated in FIG. 2) may be provided downstream of valves 2, 12 and upstream of nebuliser input 3 to facilitate rapid thorough mixing. In this case it is essential that the antagonist system be selected so that the destruction of peroxide by the antagonist is sufficiently slow that a sufficiently high concentration of peroxide is available in chamber 9 for sufficiently long to achieve a desired level of disinfection/sterilisation.

PRELIMINARY EXPERIMENTS

Various transition metal based antagonist systems, and reaction conditions, have been screened for use in embodiments of the invention. Screening was initially conducted using bulk solutions combined in a tube, rather than as aerosols. Because the destruction of peroxide by these systems is highly exothermic, temperature rise measurement in solution systems has been used as a proxy for measurement of the rate of destruction of hydrogen peroxide in aerosol in preliminary experiments 1-6.

Preliminary Experiment 1

Transition Metal Antagonist Systems

Figure 3:
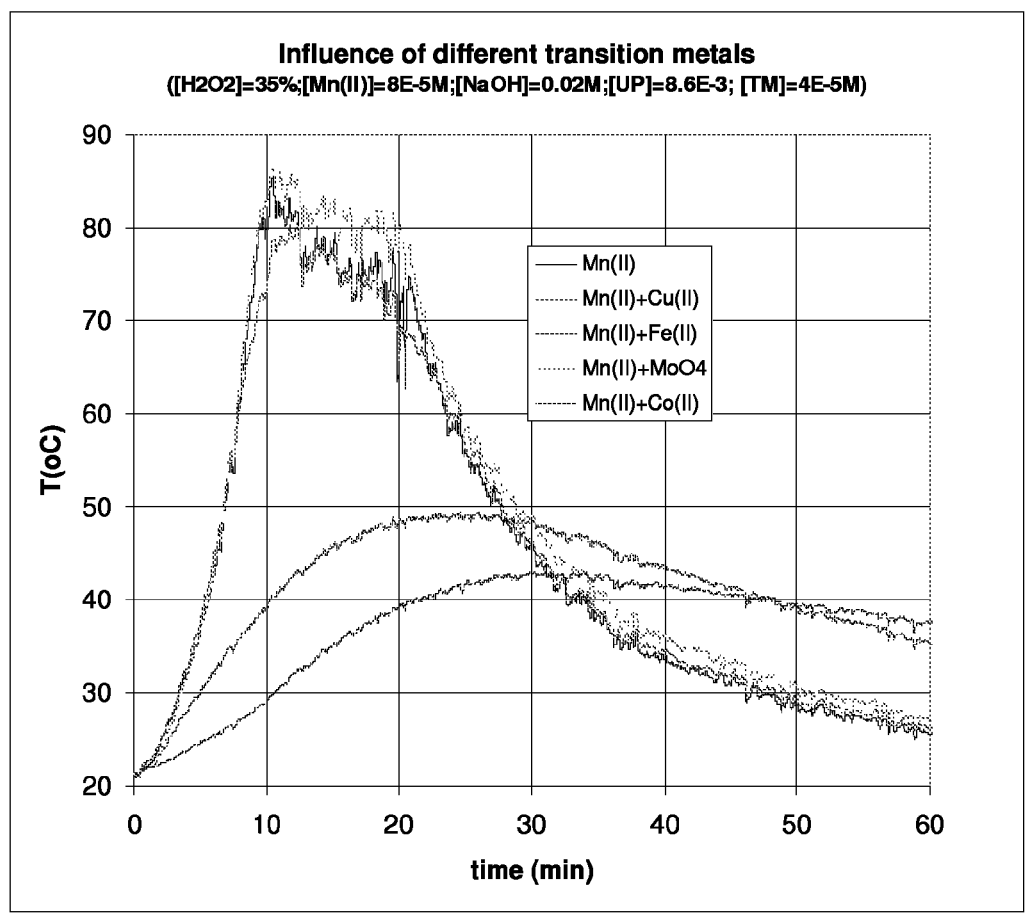
FIG. 3 is a graph showing thermal effects of hydrogen peroxide destruction in the presence of different transition metals.

FIG. 3 shows temperature as a function of time for a combination of 35% hydrogen peroxide solution in combination with the metals of Table 1 used as an antagonist (catalytic peroxide destructor) in the presence of 0.02M sodium hydroxide.

TABLE 1

| Example ID | Transition metal |
|---|---|
| 1a | Manganese (II) |
| 2a | Mn(II) + Cu(II) |
| 3a | Mn(II) + Fe(II) |
| 4a | Mn(II) + MoO$_4$ |
| 5a | Mn(II) + Co(II) |

FIG. 3 shows that manganese as Mn(II) salt or KMnO$_4$ alone gave relatively rapid results even at concentrations of below $1 \times 10^{-4}$ M, reaching a peak rate of reaction with 35% peroxide after about 10 mins. Mn has a permissible exposure limit according OH&S requirements of 5 mg/m$^3$ of Mn. Compounds of Ce, Ti, Fe, Mo and Mn can be used as promoters but salts of manganese have shown showed the most acceptable efficacy of those tested to date.

Preliminary Experiment 2

Effect of Peroxide Concentration

TABLE 2

| Example ID | Peroxide conc. |
|---|---|
| 2a | 35% |
| 2b | 50% |

TABLE 2-continued

| Example ID | Peroxide conc. |
|---|---|
| 2c | 20% |
| 2d | 15% |

Figure 4:
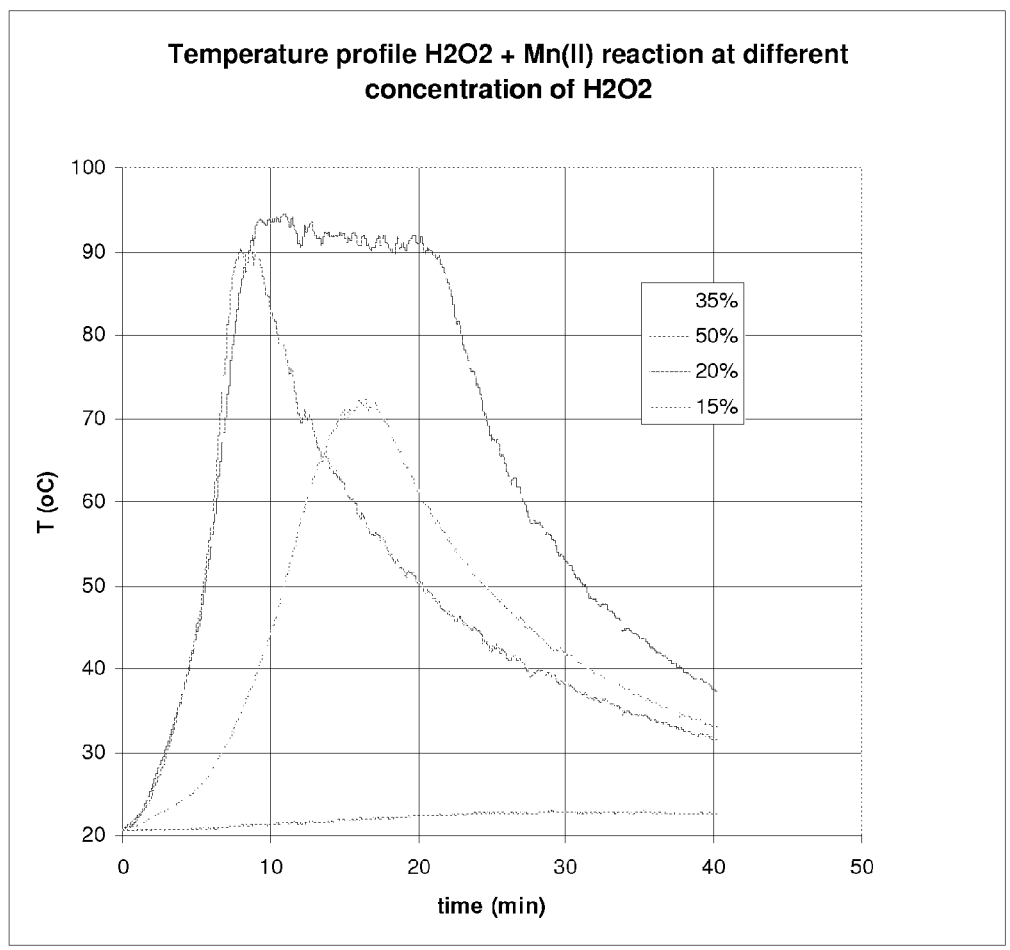
FIG. 4 is a graph showing Thermal effects $H_2O_2+Mn(II)$ reaction at different initial concentration of hydrogen peroxide ($[Mn(II)]=1.2\times10^{-4}M$).

The effect of various concentrations of peroxide as in table 2 on the reaction profile (as indicated by exothermic temperature) with a Mn(II) antagonist is shown in FIG. 4. The stability of 50% hydrogen peroxide looks unexpected but may be explained by the variation of concentration and the nature of stabilisers in solutions. 15% and 20% hydrogen peroxide solutions were prepared by dilution of 35% solution. 50 and 35% hydrogen peroxide solution were individual batches which contain different concentration and nature of additives.

Preliminary Experiment 3

Effect of Mn(II) Concentration

Figure 5:
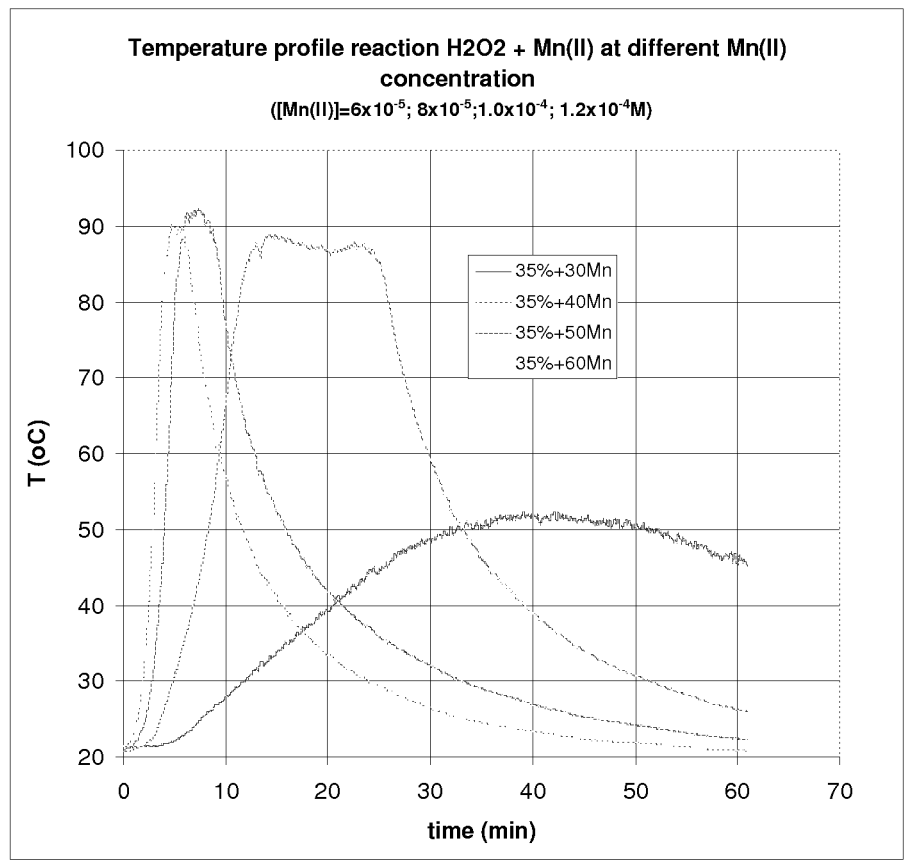
FIG. 5 is a graph showing effect of initial Mn(II) concentration on rate of $H_2O_2$ destruction.

The effect on the reaction profile of variation of initial Mn(II) concentration in a combination with 35% peroxide solution (as indicated by exothermic temperature) with an Mn(II) antagonist is shown in FIG. 5. It is clear that the rate of hydrogen peroxide destruction is very sensitive to the initial Mn(II) concentration. As a rough approximation the data of FIG. 5 gives around 1.5 order influence of Mn(II) concentration on the rate of hydrogen peroxide destruction.

Preliminary Experiment 4

Effect of Alkaline Additives and Starch

35% hydrogen peroxide solution (obtained from INTEROX—containing peroxide stabilisers)) was rather stable. It was difficult to start Mn(II)+$H_2O_2$ reaction with "native" solution and a low Mn(II) concentration. It was found that to achieve a reasonable rate of reaction the initial pH of the hydrogen peroxide solution should be increased.

Figure 6:
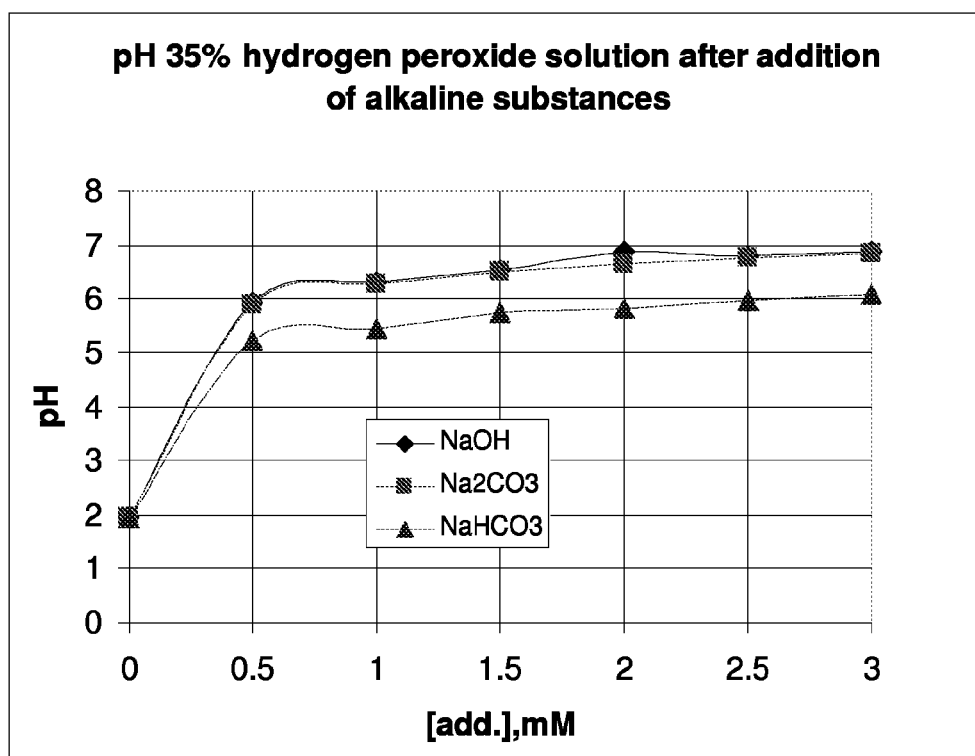
FIG. 6 is a is a graph showing the pH 35% hydrogen peroxide after addition of various alkaline substances.
Figure 7:
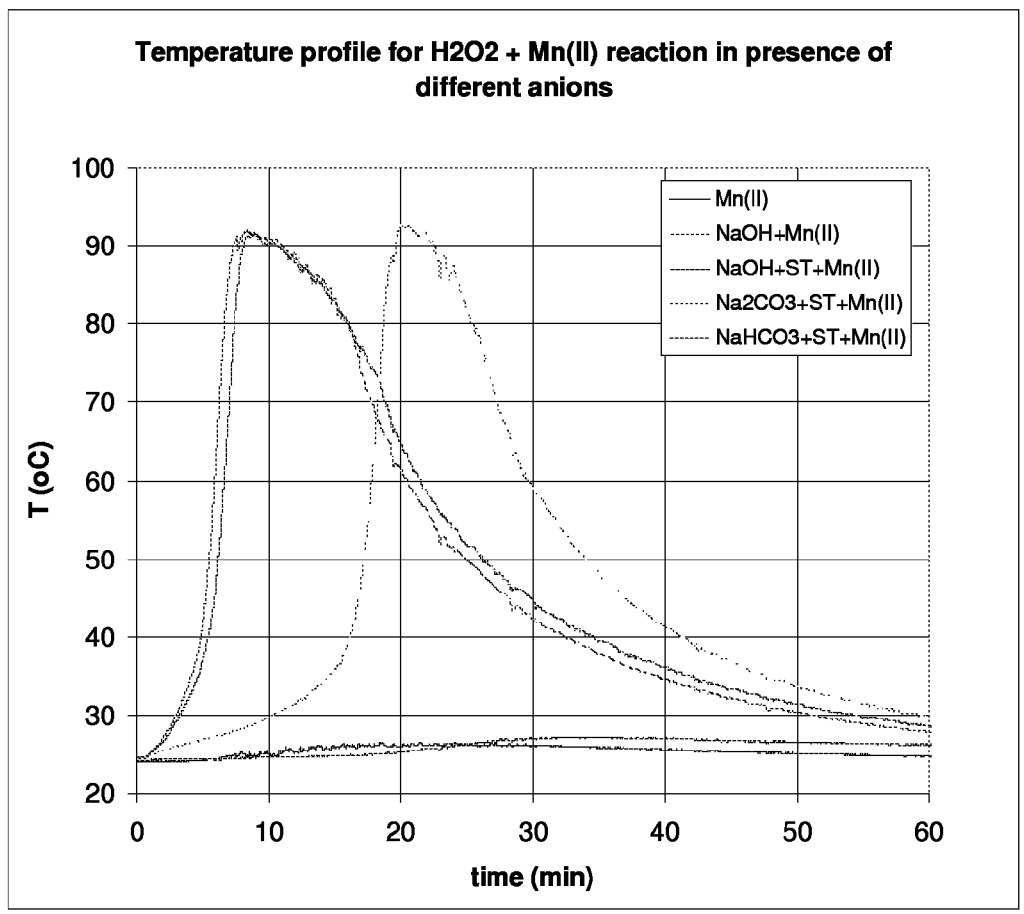
FIG. 7 is a is a graph showing the effect of nature of alkaline additives on rate of $H_2O_2+Mn(II)$ reaction. (ST—starch as a crystal-formation component).

This was exemplified with three alkaline additives: NaOH, $Na_2CO_3$ and $NaHCO_3$. The effect of changing in pH of hydrogen peroxide solution using these chemicals can be seen in FIG. 6. FIG. 7 shows the effect of those additives on the reaction profile with 35% peroxide solution (as indicated by exothermic temperature) with an Mn(II) antagonist.

The effect of alkaline additives was found to be surprising in effect, and can not be explained only by change of the pH of the solution from acidic to almost neutral. It is clear from FIG. 6 that NaOH and $Na_2CO_3$ affects changes to the pH substantially identically but the kinetic $H_2O_2$ destruction appears from FIG. 7 to be different. Addition of carbonate turned the reaction of $H_2O_2$+Mn(II) by anions into a process with a clear lag time usually typical for radical-chain reaction in the presence of inhibitors. The inventors speculate that oxidation of Mn(II) by hydrogen peroxide generates superoxide and hydroxyl radicals and that carbonate and bicarbonate ions act as scavengers of hydroxyl free radicals:—

$$HO.+HCO_3^-/CO_3^{2-} \rightarrow HCO_3./CO_3^-.+OH^-, \text{ where}$$

$$k=8.5\times10^6+3.9\times10^8\times10^{pH-10.3} M^{-1}s^{-1}$$

The mechanism reaction $H_2O_2$+Mn(II) in the presence of different additives can be much more complicated. But it appears possible that by changing carbonate concentration it is possible to create a valuable lag time (see FIG. 8). Note in FIG. 8 ST=0.01% starch It will be appreciated from FIG. 8 that by control of factors such as discussed above, it is possible to obtain an induction period of up to 10 minutes under the conditions trialled which is long enough to enable a peroxide aerosol to be highly effective as a biocide substantially before its destruction commences in earnest. Note also that peroxide may continue to act biocidally even after its destruction initiates, and that after initiation the destruction may initially still proceed slowly.

Preliminary Experiment 5

Influence of Temperature

Figure 9:
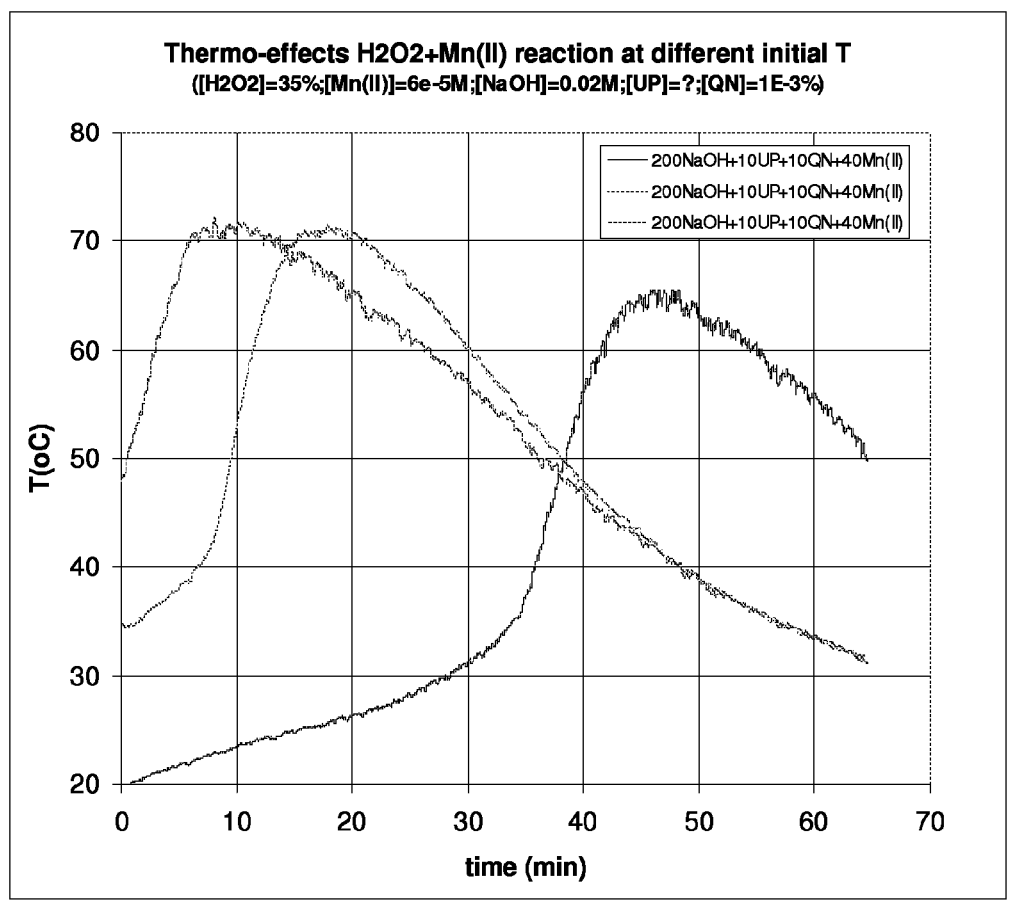
FIG. 9 is a graph showing the effect of temperature of initial solution on kinetics of hydrogen peroxide destruction.

Temperature of the reaction mixture was found to be a very powerful factor to control the rate of chemical reaction. During destruction of hydrogen peroxide by Mn(II) or permanganate in tubes the temperature of the solution rather often reached boiling point. This should not happen when the biocide is sprayed as a mist due to absolutely different heat exchange conditions in bulk solution and in a thin layer of biocide. However, the initial temperature of the solution can be a parameter which can help to control lead time as shown in FIG. 9 which shows the effect of temperature of initial solution on kinetic of hydrogen peroxide destruction. By lead time is meant the lag or induction period before the reaction velocity increases steeply. A lower temperature of the initial solution leads to a longer lead time. By varying the temperature of initial solution, the length of lead time of Mn(II)+$H_2O_2$ reaction can be controlled without compromise of its efficacy. With an initial temperature of 2° C. under the conditions shown in FIG. 9 lead times of more than 30 mins were obtainable.

Preliminary Experiment 6

Influence of Other Additives

Figure 10:
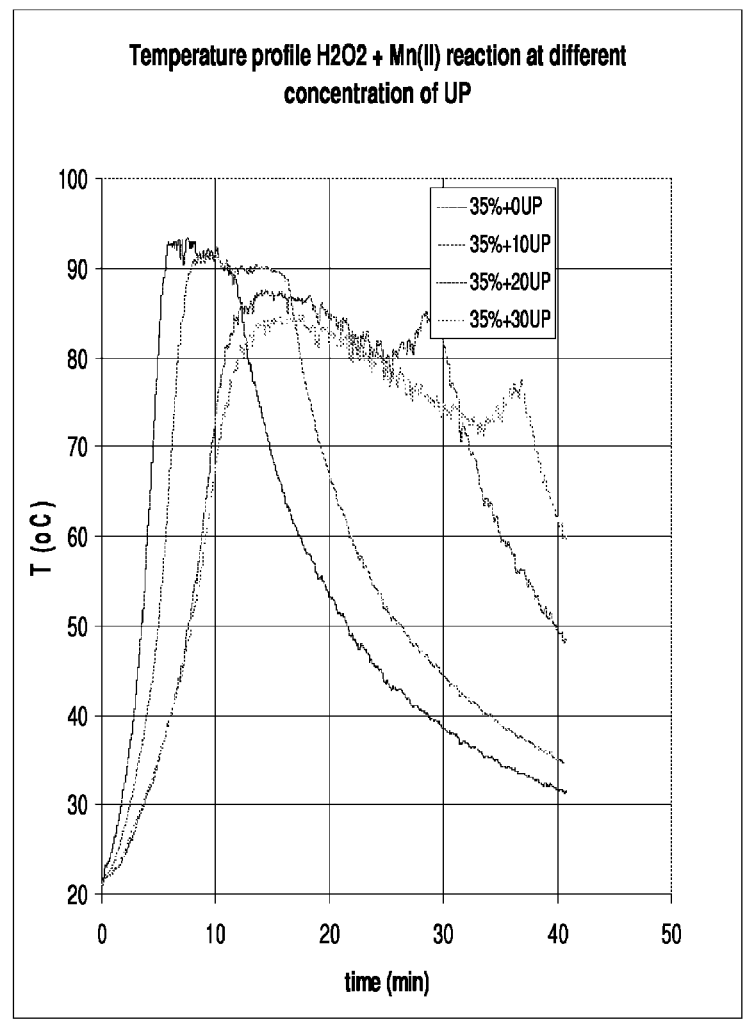
FIG. 10 is a graph showing the influence of various urea-peroxide combinations on kinetics of $H_2O_2+Mn(II)$ reaction.
Figure 11:
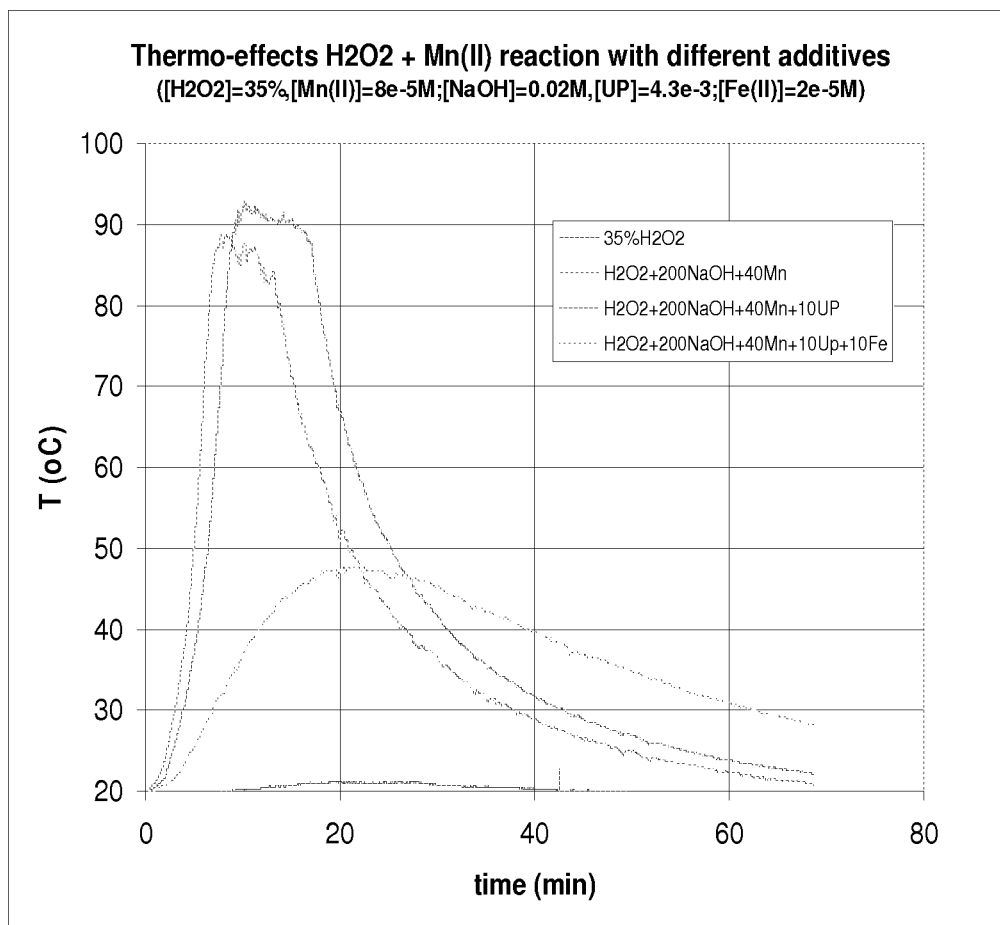
FIG. 11 is a graph showing the influence of urea-peroxide combination on kinetic $H_2O_2+Mn(II)$ reaction.

Starch was added as a stabilizer of colloidal solution of $MnO_2$ and appeared to extend the range of additives which can help to control the reaction's parameters. FIGS. 10 and 11 show the effect of urea-peroxide on the kinetics of $H_2O_2$+Mn(II) reaction.

Example 1

Examples of Self Destructive Biocidal Aerosol According to the Invention

Various modifications of a Self Destructive Biocide ("SDB") aerosol were prepared by combining hydrogen peroxide of various concentrations (ranging from 10% to 35%) with an antagonist consisting of various concentrations of $Mn(NO_3)_2$ in the presence of sodium carbonate and 0.01% starch and producing an aerosol from the combination immediately after mixing.

Bench testing of hard surface carriers for different microorganisms was carried out.

Some results are presented in Tables 3 and 4. Glass slides were inoculated with *Geobacillus stearothermophilus* (1×1 cm area) and PES slides were inoculated with *Bacillus subtilis* spores (2×2 cm). In each case 60 μL of SDB aerosol were spread on top of the inoculated area and exposed for a predetermined time with various SDB aerosols (specifically the four biocidal preparations identified in Table 3 which accord to the sixth aspect of the invention). Effectiveness of aerosols of corresponding concentrations of hydrogen peroxide alone are also shown in table 3 for comparison

TABLE 3

Results of bio-efficacy testing, using EN hard surface Standard for
*Geobacillus stearothermophilus* on glass slides 1 × 1 cm inoculation area).
Control ~1 × 10⁵ CFU

| Biocide | exposure time (min) and $\log_{10}$ reduction | | | |
|---|---|---|---|---|
| | 5 | 10 | 15 | 20 |
| 35% $H_2O_2$ + 0.02M $Na_2CO_3$ + 0.01% starch + 1.2e-4M Mn(NO$_3$)$_2$ | 5/2.4 | 5/5 | n/a | n/a |
| 19.1% $H_2O_2$ + 0.02M $Na_2CO_3$ + 0.01%starch + 1.2e-4M Mn(NO$_3$)$_2$ | 2.8/3.2 | 5/4.7 | n/a | n/a |
| 14.5% $H_2O_2$ + 0.02M $Na_2CO_3$ + 0.01%starch + 1.2e-4M Mn(NO$_3$)$_2$ | n/a | 3.3/3.2 | 3.7/3.9 | 3.9/3.2 |
| 10% $H_2O_2$ + 0.02M $Na_2CO_3$ + 0.01%starch + 1.2e-4M Mn(NO$_3$)$_2$ | n/a | n/a | 2.5/2.3 | 2.8/2.8 |
| 35% $H_2O_2$ | 5.9/5.0 | n/a | n/a | n/a |
| 19.1% $H_2O_2$ | n/a | 2.8/3.1 | n/a | n/a |
| 14.5% $H_2O_2$ | n/a | 3.5/2.3 | 2.4/3.3 | n/a |
| 10% $H_2O_2$ | n/a | n/a | 0.5/0.0 | 2.3/2.3 |

In Table 3, a 5 log reduction approximates total kill and was achieved by samples using 35% peroxide within 5 mins, the same as in the absence of antagonist. Surprisingly, the 19.1% peroxide achieved a higher level of kill in the presence of the antagonist than in its absence, achieving 4.7 log reduction within 10 mins. Table 4 shows that at all peroxide concentrations greater than 19%, greater than 7 log reduction (substantially total kill) of difficult to destroy *B. subtillis* in the presence of the antagonist could be achieved by the aerosol in less than 5 mins, and at peroxide concentrations in the 19-35% range the aerosol achieved greater than 7 log reduction in less than 5 mins (ie in the presence of the antagonist).

Table 4 shows the results of a similar test using *B. subtillis* on PEC slides.

TABLE 4

Results of bio-efficacy testing using *Bacillus subtilis* on PEC slides
(area 2 × 2 cm). 60 μL of biocide was placed on each sample.
Control 2 × 10⁷ CFU

| | Exposure time and Log10 reduction | | |
|---|---|---|---|
| | 5 min | 10 min | 15 min |
| 35% $H_2O_2$ + 0.02M NaOH + 0.01% starch + 1.2e-4M Mn(NO$_3$)$_2$ | 4.5 | 4.1 | 7.4 |
| 35% $H_2O_2$ + 0.02M $Na_2CO_3$ + 0.01% starch + 1.2e-4M Mn(NO$_3$)$_2$ | 7.4 | 7.4 | 7.4 |
| 35% $H_2O_2$ + 0.02M NaHCO$_3$ + 0.01% starch + 1.2e-4M Mn(NO$_3$)$_2$ | 7.4 | 7.4 | 7.4 |
| 19.1% $H_2O_2$ + 0.02M $Na_2CO_3$ + 0.01% starch + 1.2e-4M Mn(NO$_3$)$_2$ | 7.4 | ? | 7.4 |
| 14.5% $H_2O_2$ + 0.02M $Na_2CO_3$ + 0.01% starch + 1.2e-4M Mn(NO$_3$)$_2$ | 1.9 | 1.7 | 2.4 |

The SDB aerosol destroyed itself within from 40 to 60 minutes, ie the peroxide residues were converted to oxygen and water. It will be appreciated that experiments conducted to date have been directed at proof of principle and the data herein does not necessarily represent the shortest destruction time achievable, or the optimum conditions. However, since the destruction time does not depend on replacing volumes of air, this indicates that the same short time to remove peroxide could be obtained using a self destructive biocidal aerosol in a space of thousands of square meters in a warehouse as easily as in a half cubic meter glove box. The SDB aerosol contains the seeds of its own destruction and does not need to be transported to a "destructor" or be transported to be rendered innocuous Efficacy of SDB examples with *Staphylococcus aureus* were tested slightly differently. PES slides were inoculated with *Staphylococcus aureus* (2×2 cm) and different amounts of tested biocide were spread on the top of inoculated area. A small MATRIX was used where variables were—concentration of hydrogen peroxide (35, 19 and 14.7%), dosage (30, 40, 50 and 60 μL of biocide), exposure time (5 and 10 min).

Figure 12:
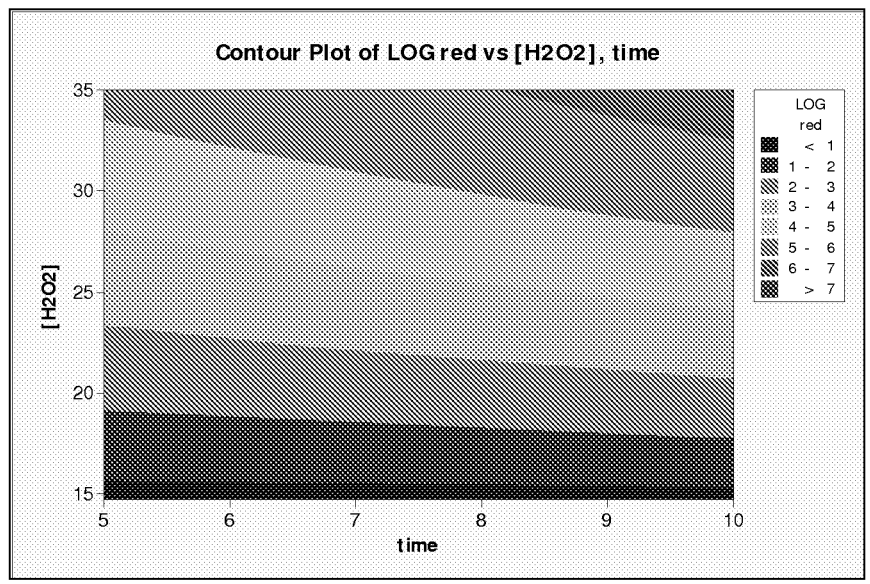
FIG. 12 is a graph showing the effect of hydrogen peroxide concentration and exposure time on Log 10 reduction of *Staphylococcus aureus*.
Figure 13:
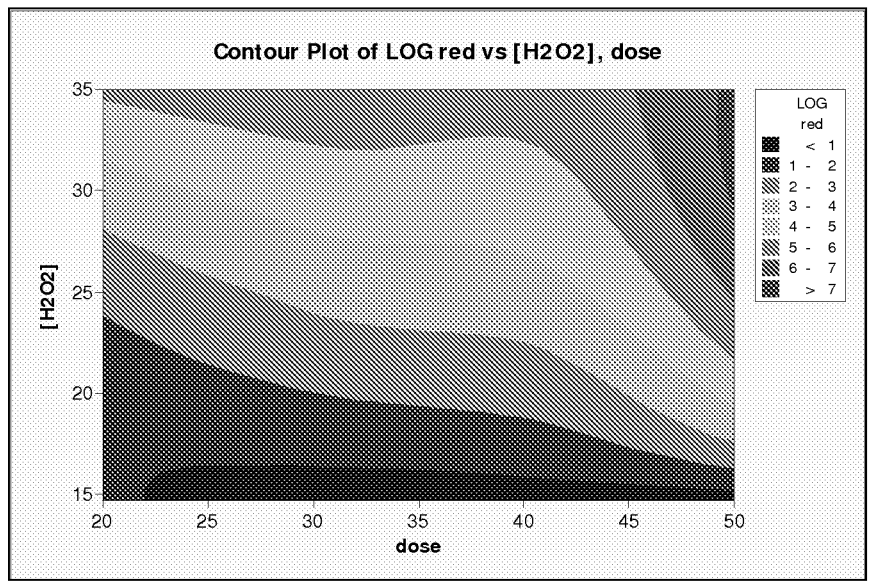
FIG. 13 is a graph showing the effect of hydrogen peroxide concentration and exposure time on Log 10 reduction of *Staphylococcus aureus*.
Figure 14:
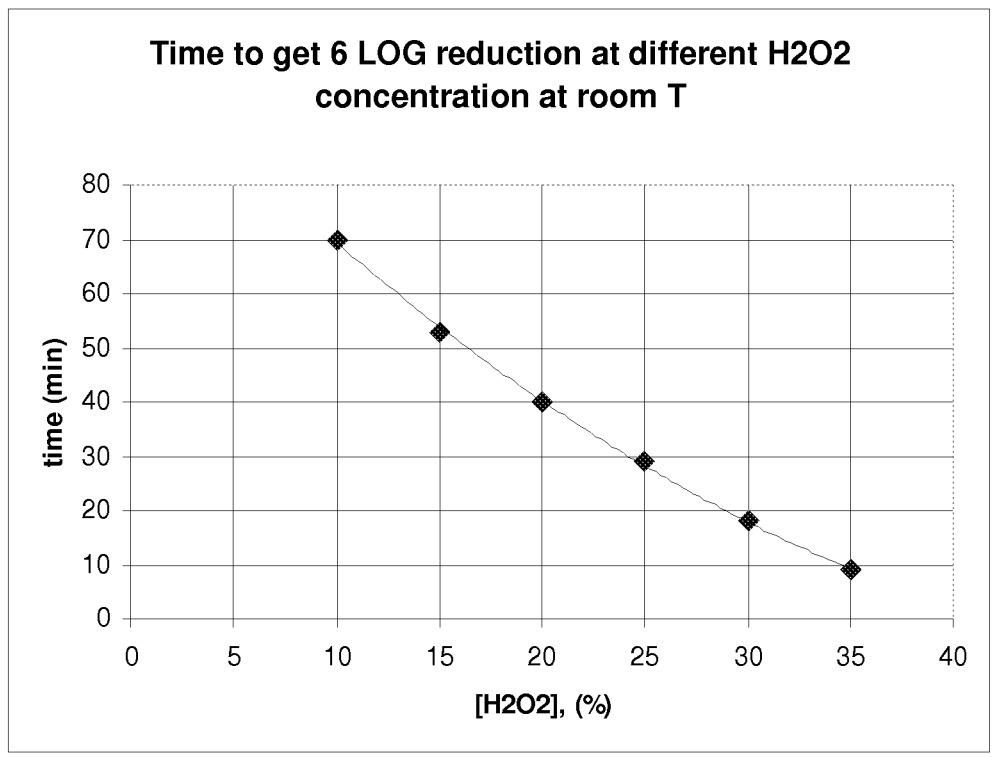
FIG. 14 is a graph showing the Time required to achieve 6 log reduction of *Staphylococcus aureus* on PES slide using SDB.

The results of this MATRIX as three-dimensional graphs are presented in FIGS. 10 and 12 and 13. FIG. 14 shows the time required to achieve a log 6 reduction in *S. aureus* on a PES slide using an SDB aerosol. It can be seen from FIG. 14 that SDB works approximately like hydrogen peroxide aerosol alone or even slightly better. The antagonist additives according to the invention which converted hydrogen peroxide into a self-destructive composition do not reduce its biocidal efficacy, but rather enhance it, and this mixture can be used as an improved biocide with additional self-destructive properties.

Several experiments were undertaken to prove that the concept of "self-destructive biocide" (SDB) really works in "in use" conditions. Firstly the SDB disintegration was checked when it was deposited on polymer (PES) or glass slides.

The test was undertaken using following procedure:
1. 60 μL of SDB (usually mixture of hydrogen peroxide, Mn(II), starch or other additives) straight after mixing was deposited from an aerosol on the surface of PES at room temperature.
2. Each slide of PES with SDB after certain exposure time was transferred to conic flask with diluted sulfuric acid for titration of hydrogen peroxide residual left over.

Figure 15:
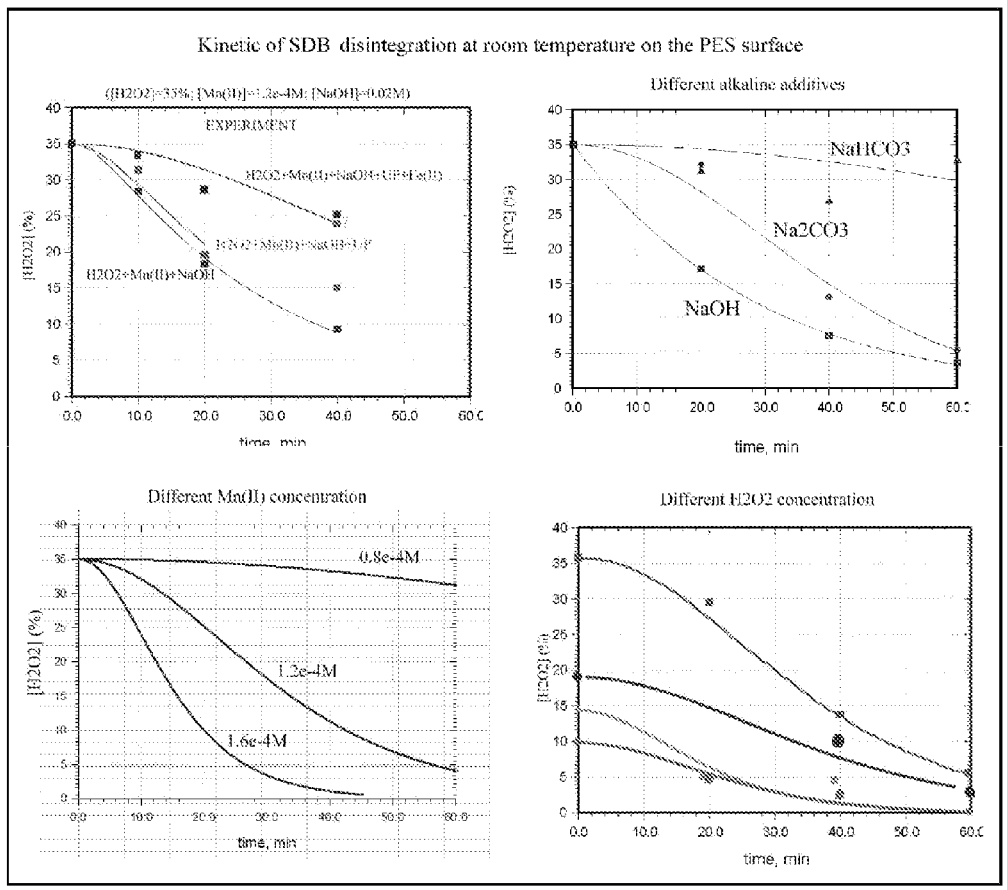
FIG. 15 is a set of graphs showing the kinetic SDB disintegration on a PES surface at different conditions.

Some results are presented in FIG. 15.

Figure 8:
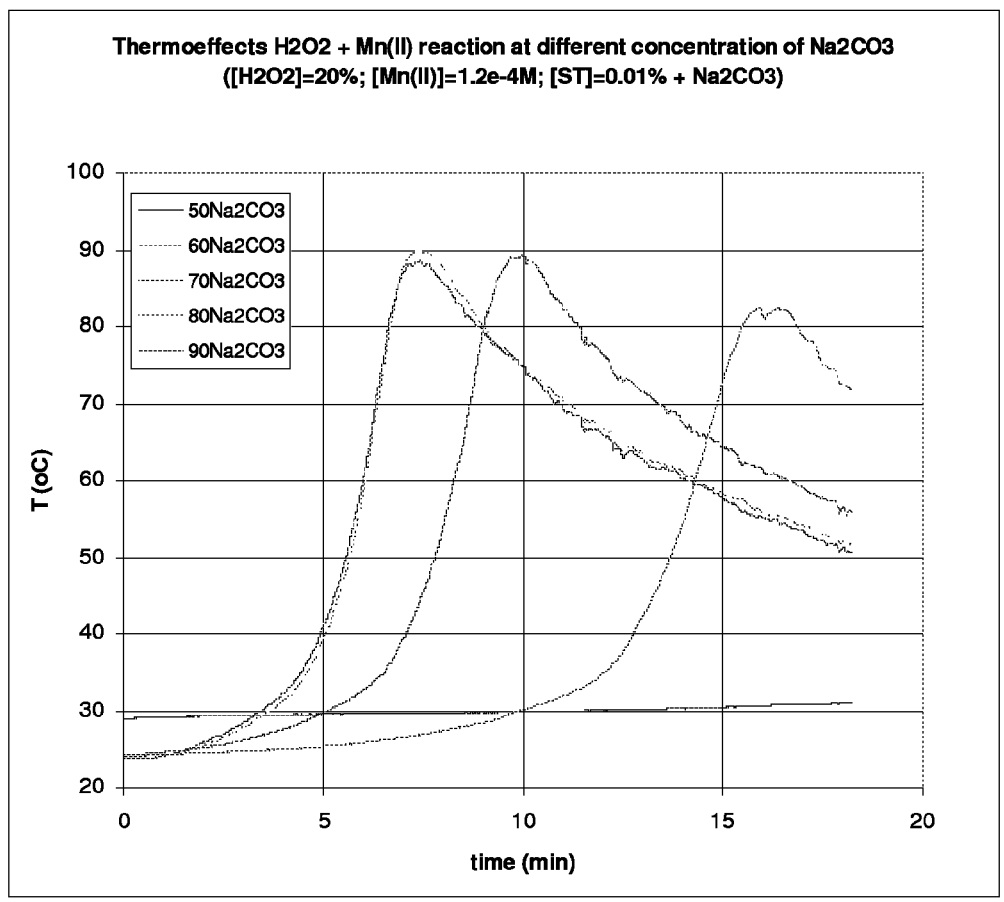
FIG. 8 is a is a graph showing the effect of carbonate concentration on thermo-effect of $H_2O_2+Mn(II)$ reaction.

If the result of SDB aerosol destruction on the PES surface is compared with kinetic SDB destruction as a bulk liquid it can be concluded that the absolute value of destruction rate of SDB aerosol on the surface was much lower compared than in bulk solution. This decline in the rate of reaction was attributed to differences in heat dissipation. But at the same time the trends in different additives influence and effects of the concentration of main components were substantially the same. For example, increasing Mn(II) concentration leads to increasing SDB aerosol destruction rate (see FIGS. 5 and 15*c*). Different alkaline additives can increase or decrease destruction rate and again bicarbonate on the surface and in bulk solution decreases the destruction rate and carbonate creates some lag time (FIGS. 8 and 15*b*). Addition of Fe(II) to SDB in both cases decreases the destruction rate (see FIGS. 11 and 15*a*).

Figure 16:
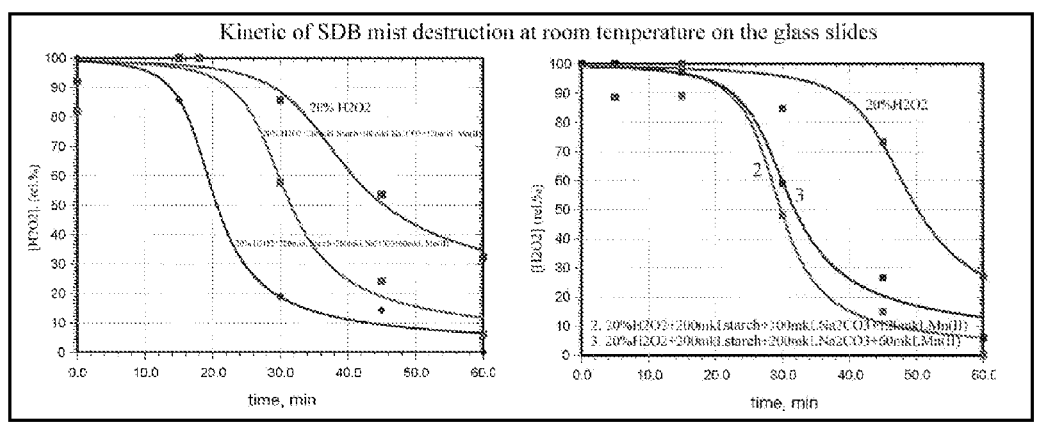
FIG. 16 is a set of graphs showing SBD mist destruction on glass slides surface at room temperature.

The effect of thin layer deposition of SDB aerosol on its behavior was examined. In this case straight after mixing of components, SDB was transferred into a standard nebuliser. Mist of SDB was deposited for 5 min on glass slides at room temperature. After a certain time the glass slide was transferred into a conic flask with diluted sulfuric acid for titration. The results are presented in FIG. 16.

The behavior of SDB aerosol in this case differs from the situation with bulk solution and big droplet deposition. First of all there is evidence of evaporation of mist from the surface in time (curve 20% $H_2O_2$ without any additives). Secondly a positive effect of additives on the destruction rate of hydrogen peroxide can be observed.

So far the invention has been exemplified primarily with reference to hydrogen peroxide as the biocide. Those skilled in the art will recognize from the teaching hereof that peroxides other than hydrogen peroxide may be employed as the biocide without departing from this invention for example t-butyl hydroperoxide, or urea hydrogen peroxide or polyvinylpyrrolidone hydrogen peroxide. Moreover, the invention is applicable to biocides other than peroxides for example other oxidizing agents such as ozone, permanganate, perchromate, oxy halides, per-acetic acid, per-citric, per-ascorbic, per-formic acid, perborates, percarbonates, ethylene oxide, chlorine dioxide, and combinations of oxidizing agents (optionally activated by "bleach activators" such as for example acetyl choline chloride, monoacetin, diacetin).

In addition, non oxidizing biocides such as biocidal quats, silanols, glycols, halogenated phenols, polyvinylpyrrolidone iodine complexes and the like may be chosen in combination with suitably selected antagonists.

It will also be recognized by those skilled in the art from the teaching hereof that antagonists other than those so far exemplified for peroxides may be employed including all those known for use in catalytic destructors for peroxides and including (but not limited to) other metal catalysts such as iron, copper, cobalt, vanadium, nickel, chromium, manganese, osmium and silver, titanium, metals of the platinum group, metal ions, inorganic oxides and anhydrides, or salts, or combinations of the foregoing; amines such as triethanolamine or diethylenetriamine, and other suitable bases such as for example alkali metal hydroxides, suitable oxy halide compounds MOX (wherein M is an alkali metal, O is oxygen, X is a halogen—for example NaOCl), sulfides, alcohols and other compounds known to react with peroxides either as reducing or oxidizing agents, as well as suitable enzymes such as catalases, and the like. Suitable antagonists may be formed in situ by reaction in the droplets from precursors and the kinetics of the formation reaction may be used to increase the induction time or affect the kinetics of reaction between biocide and antagonist. The antagonist need not be in liquid form but may be aerosolized as a suspension of microfine solid either formed in situ or nebulised as a suspension in a liquid carrier.

Figure 17A:
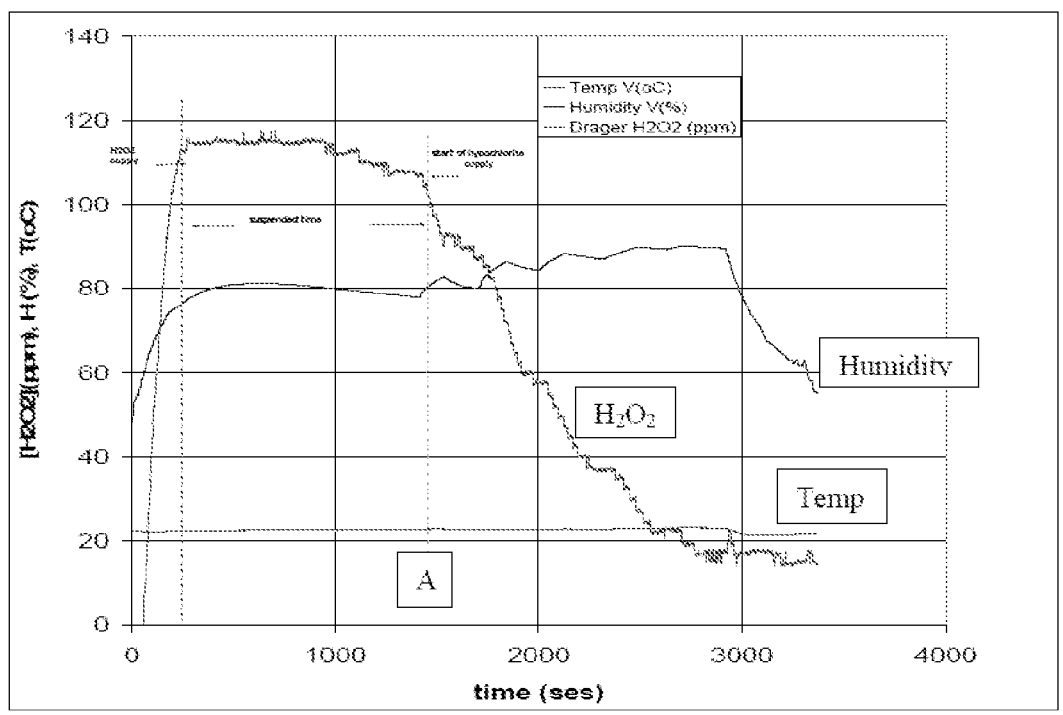
FIG. 17 is a set of graphs showing the time required for inactivation of hydrogen peroxide nebulant by sodium hypochlorite nebulant (separately nebulised) as antagonist.
Figure 17B:
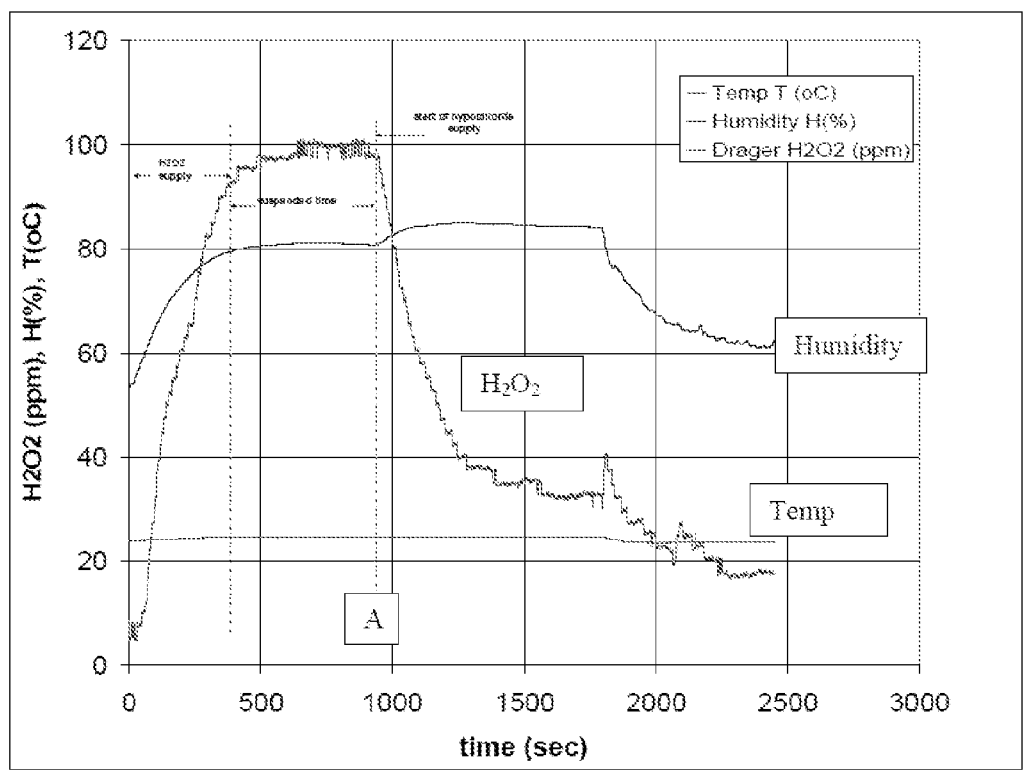

A further example of the invention is illustrated in FIGS. 17a and 17b. The peroxide concentration, relative humidity and temperature are shown as a function of time. A solution of hydrogen peroxide (35%) was admitted as an aerosol to a chamber from a first nebuliser as a biocidal nebulant, and NaOCl solution (4%) was admitted as a nebulised antagonist from a second nebuliser after at time "A", which was about 200 seconds in the case of FIG. 17a and about 400 seconds in the case of FIG. 17b. The droplets combine and the following reaction occurs:

$$NaOCl + H_2O_2 \rightarrow NaCl + H_2O + O_2$$

In the example of FIG. 17a, the peroxide concentration was around 120 ppm within 1500 seconds but was reduced by the reaction with NaOCl to less than 20 ppm within a further 1500 seconds. In the example of FIG. 17b, the peroxide concentration was around 100 ppm within 1000 seconds but was reduced by the reaction with NaOCl to less than 20 ppm within a further 1500 seconds. Significantly both peroxide and NaOCl have biocidal properties and the products, NaCl, $H_2O$ & $O_2$ are harmless. Note that the NaOCl could be used as the biocide and the peroxide as the antagonist or vice versa.

In a further example peracetic acid as the biocide was combined with hypochlorite at pH adjusted to 6-8 as the antagonist. The combination was immediately nebulised and used as a sporicidal biocidal nebulant. The nebulant was biocidally effective before the hypochlorite neutralised the peracetic acid. At pH 6-8 free chlorine produced is converted to hypochlorous acid and the biocidal efficacy is enhanced with a surprising degree of reduction in the odour usually experienced when peracetic acid is used as a biocide. If preferred the peracetic acid and hypochlorite can be nebulised separately and subsequently combined. Examples like this in which both the biocide and antagonist have biocidal properties but neutralize one another are particularly favoured for use in the invention. Those skilled in the art will be able to select conditions so that the combination will have sufficient time to be biocidally effective before neutralization is complete.

In yet another example, the self-inactivating aerosol composition according to the present disclosure comprises a pH adjusting compound. In certain embodiments, the pH adjusting compound is a basic compound. Nonlimiting examples of basic compounds include hydroxides, hypochlorites, carbonates, and bicarbonates. In certain embodiments, the pH of the self-inactivating aerosol composition is 5 or greater, such as a pH between about 6 and 7.

Combinations of peroxide, peracetic acid and hypochlorite have been found to be particularly effective as biocides and to form harmless residues on inactivation.

Suitable antagonists can be selected from among oxidizing agents and reducing agents for other biocides.

In a further example, Fenton's reaction (and analogues thereof) can also be employed in the present invention. For example an iron catalyst as a solution of $FeSO_4$ may be combined with the hydrogen peroxide (typically 1 part of Fe per 5-25 parts hydrogen peroxide) immediately prior to nebulizing the solution or may be nebulised separately and the iron sulfate nebulant mixed with the peroxide nebulant:

$$Fe^{2+} + H_2O_2 \rightarrow Fe^{3+}.OH(radical) + OH^-$$

$$Fe^{3+} + H_2O_2 \rightarrow Fe^{2+}.OOH(radical) + H^+$$

The hydroxyl radicals can then be utilized as an antagonist via addition reactions as exemplified by reaction with benzene:

$$OH + C_6H_6 \rightarrow (OH)C_6H_6$$

or via hydrogen abstraction as exemplified by reaction with methanol:

$$OH + CH_3OH \rightarrow CH_2OH + H_2O$$

or via electron transfer or radical reactions.

These reactions have not previously been conducted with reagents combined as aerosols.

Modifiers affecting the kinetics of the reaction between the antagonist and the biocide are not limited to those herein exemplified.

The aerosol may be generated and distributed by any suitable means. The carrier gas need not be air but could be nitrogen, an inert gas or other suitable medium. Although the hydrogen peroxide has been herein described with reference to its biocidal properties, it has other uses and the invention may be equally applicable to elimination of residual peroxide when used for such other uses, eg bleaching. It is envisaged that self destructing combinations of hydrogen peroxide and per acetic acid will have particular application for disinfection/sterilization in the food and food processing industries.

In yet another example the biocide may be a biocidal quaternary ammonium compound, for example dodecyldimethyl ammonium chloride, chlorhexidine gluconate or benzyl ammonium salts, and in that case the antagonist is may be, for example, an anionic compound or anionic detergent exemplified by a dodecyl benzene sulfonic acid.

In yet another example the biocide may be based on a biocidal silanol terminated silanes and siloxanes, for example triethylsilanol or diphenylmethylsilanol, and the antagonist may be an oxidizing agent or esterifying acid. If the biocide is an acid then the antagonist may be a base or vice versa.

Use of other biocides, use of other antagonists and selection of suitable combinations thereof will be obvious to those skilled in the art from the description herein contained and such variations are deemed to lie within the inventive concepts herein disclosed.

The claims defining the invention are as follows:

1. A method of disinfection comprising the steps of:
   (i) allowing an aerosol to contact a first concentration of microorganisms for a sufficient time to achieve a reduction in the concentration to a lower level than the first, wherein the aerosol comprises droplets dispersed in a carrier gas, wherein at least some of the droplets contain a peroxide biocide; and at least some of the droplets in the aerosol contain an antagonist reactive with the peroxide biocide to render it harmless by decomposition of the peroxide biocide, wherein
      (a) the aerosol comprises suspended droplets of the peroxide biocide and the antagonist, whereby decomposition of the peroxide biocide occurs when droplets of the peroxide contact droplets of the antagonist as a result of collision, coalescence or condensation, or
      (b) at least some of the droplets contain both the peroxide biocide and the antagonist,
   whereby the reaction kinetics of the peroxide biocide and the antagonist are controlled so that the biocide is effective to kill microorganisms before the biocide is decomposed by the antagonist; and
   (ii) allowing the antagonist to inactivate any remaining peroxide biocide.

2. A method according to claim 1, wherein the peroxide is hydrogen peroxide or peracetic acid.

3. A method according to claim 1, wherein the peroxide is hydrogen peroxide and is rendered harmless at a concentration below 1 ppm.

4. A method according to claim 1, wherein the peroxide biocide is used for disinfection, and the nature and concentration of the antagonist is selected, or means are provided, to ensure that the time required for the antagonist to render the peroxide biocide ineffective is longer than the time required for the peroxide biocide to be effective for a desired level of disinfection.

5. A method according to claim 1, wherein the peroxide biocide, decomposition by the antagonist proceeds at a slower rate than the biocide's disinfection rate.

6. A method according to claim 1, wherein the aerosol further comprises at least one additional biocide selected from the group consisting of biocidal oxidizing agents, quaternary ammonium compounds, aldehydes, halogenated phenols, silanols, and combinations thereof.

7. A method according to claim 6, wherein the biocidal oxidizing agent is selected from the group consisting of oxyhalogen compounds, metal oxyhalides, perhalogenates, ozone, hydroxyl radicals, and combinations thereof.

8. A method according to claim 1, wherein the antagonist is selected from the group consisting of metals, metal ions, metal oxides, oxidizing agents, reducing agents, amines, anionic detergents and enzymes effective to decompose the selected biocide or biocidal combination, and combinations thereof.

9. A method according to claim 8, wherein the antagonist is selected from the group consisting of oxidizing agents and oxidizing agents in combination with metal ions effective to inactivate the biocide.

10. A method according to claim 1, wherein the biocide comprises a peroxide and the antagonist comprises a metal, metal ion, or metal oxide, or combination thereof.

11. A method according to claim 10, wherein the metal is Mn(II).

12. A method according to claim 1, wherein the antagonist is produced in situ in the aerosol by reaction between antagonist precursors.

13. A method according to claim 1, wherein the peroxide concentration prior to decomposition is 35%.

14. A method according to claim 1, wherein the aerosol further comprises a pH adjusting compound.

15. A method according to claim 14, wherein the pH adjusting compound is a basic compound.

16. A method according to claim 15, wherein the basic compound is selected from the group consisting of a hydroxide, a hypochlorite, a carbonate, a bicarbonate, and combinations thereof.

17. A method according to claim 1, wherein the pH is 5 or greater.

18. A method according to claim 17, wherein the pH is between about 6 and 7.

19. A method according to claim 1, further comprising a stabilizing agent for the antagonist.

20. A method according to claim 19, wherein the stabilizing agent is starch.

* * * * *